(12) United States Patent
Belousov et al.

(10) Patent No.: US 8,357,301 B2
(45) Date of Patent: Jan. 22, 2013

(54) CHROMATOGRAPHY EQUIPMENT CHARACTERIZATION

(75) Inventors: Anton Belousov, Penzberg (DE); Thomas Dams, Pullach (DE); Benjamin Gerwat, Weilheim i. OB (DE)

(73) Assignee: Hoffmann-La Roche, Inc., Nutley, NJ (US)

( * ) Notice: Subject to any disclaimer, the term of this patent is extended or adjusted under 35 U.S.C. 154(b) by 0 days.

(21) Appl. No.: 13/380,382

(22) PCT Filed: Jun. 22, 2010

(86) PCT No.: PCT/EP2010/003813
§ 371 (c)(1),
(2), (4) Date: Apr. 24, 2012

(87) PCT Pub. No.: WO2010/149367
PCT Pub. Date: Dec. 29, 2010

(65) Prior Publication Data
US 2012/0202978 A1  Aug. 9, 2012

(30) Foreign Application Priority Data
Jun. 24, 2009 (EP) .................................... 09008247

(51) Int. Cl.
*B01D 15/08* (2006.01)
(52) U.S. Cl. ............... 210/656; 210/198.2; 530/413; 702/30; 702/84
(58) Field of Classification Search ............ 210/635, 210/656, 657, 659, 143, 198.2; 702/30, 81, 702/84, 104; 530/413
See application file for complete search history.

(56) References Cited

U.S. PATENT DOCUMENTS
6,456,955 B1 * 9/2002 Andrews et al. ............. 702/104
(Continued)

FOREIGN PATENT DOCUMENTS
WO  02/47009  6/2002

OTHER PUBLICATIONS
Sarker et al., "Study of the packaging behavior of axial compression columns for preparative chromatography" Journal of Chromatography A 702:27-44 (1995).
Larson et al., "Use of Process Data to Assess Chromatographic Performance in Production-Scale Protein Purification Columns" Biotechnol 19(2):485-492 (2003).

(Continued)

*Primary Examiner* — Ernest G. Therkorn
(74) *Attorney, Agent, or Firm* — Janet M. Martineau (57) ABSTRACT

Herein is reported a method for determining whether a re-useable chromatography column packing, which is used at least for the second time in a purification step of a purification of a polypeptide, has reduced separation efficacy in said purification step of said purification of said polypeptide, comprising the following steps: a) identifying and determining the experimental data of an inert change of at least one physicochemical parameter of a mobile phase passing through said re-useable chromatography column packing, b) determining the parameters of a function of formula I by fitting the experimental data of the inert change of the physicochemical parameter of the at least second use, c) determining the difference between the experimental data of the inert change of the physicochemical parameter of the at least second use and the function of formula I with the parameters determined in step b), d) calculating the difference between the maximum value and the minimum value of the difference determined in step c) and normalizing said difference, e) determining reduced separation efficacy of said re-useable chromatography column packing when the absolute value of the difference calculated in step d) is more than 0.1.

18 Claims, 8 Drawing Sheets

U.S. PATENT DOCUMENTS

| | | | | |
|---|---|---|---|---|
| 7,132,053 B2 * | 11/2006 | Hauck et al. | .................. | 210/656 |
| 7,267,765 B2 * | 9/2007 | Hauck et al. | ............... | 210/198.2 |
| 7,890,285 B2 * | 2/2011 | Manfredi | ...................... | 702/120 |
| 8,163,177 B2 * | 4/2012 | Van Pelt | ..................... | 210/198.2 |
| 2010/0084344 A1 * | 4/2010 | Lihme et al. | .................. | 210/656 |
| 2011/0147312 A1 * | 6/2011 | Cunnien et al. | ............... | 210/656 |

OTHER PUBLICATIONS

Moscariello et al., "Charaterizing the performance of industial-scale columns" Journal of Chromatography A 908:131-141 (2001).

Vink et al., "Resolution and Column Efficiency in Chromatography" Journal of Chromatography 69:237-242 (1972).

* cited by examiner

CHROMATOGRAPHY EQUIPMENT CHARACTERIZATION

CROSS REFERENCE TO RELATED APPLICATIONS

This application is a National Phase filing under 35 U.S.C. §371 of International Application No. PCT/EP2010/003813 having an international filing date of Jun. 22, 2010, the entire contents of which are incorporated herein by reference, and which claim benefit under 35 U.S.C. §119 to European Patent Application No. 09008247.0 filed Jun. 24, 2009.

The herein reported method is in the field of chromatography, especially in the field of preparative column chromatography. It is herein reported a method for the direct determination of the quality of the packing of a chromatography column based on in process data. With this method a saving in process time and resources can be achieved as an additional data acquisition solely for the purpose of column integrity determination can be eliminated.

BACKGROUND OF THE INVENTION

Today almost all polypeptides used in medicaments are prepared recombinantly. Due to strict regulatory guidelines and requirements by-products have to be removed from the therapeutic polypeptide preparation as much as possible. Therefore, at least one chromatography step is employed in down stream processing of the bulk raw polypeptide after recombinant production. As the dimension of the chromatography equipment with respect to the yield of the fermentation process, especially the separation capacity of chromatography columns, is limited, a multitude of batches have to be processed in order to be able to provide the required amount of purified therapeutic polypeptide.

To ensure that each batch of the purified therapeutic polypeptide has the same pharmaceutical effect, a list of analytical parameters has to be fulfilled for each batch. This can only be achieved if the steps of the purification process operate consistently and efficiently. But, if one step of the purification process does not work properly the obtained product will most probably not pass the analytical tests and, in the worst case, this batch cannot be used. Therefore, it is necessary to provide methods for determining the performance and efficacy of purification steps.

Teeters, M. A. and Quinones-Garcia, I. (J. Chrom. A 1069 (2005) 53-64) report the evaluating and monitoring the packing behavior of process-scale chromatography columns by using the responses to conductivity-based pulse and step inputs derived from tracer experiments and in-process transitions, especially from measured residence time distributions. Norling et al. (Norling, L., et al. J. Chrom. A 1069 (2005) 79-89) report the impact of multiple re-use of anion-exchange chromatography media on virus removal. The use of process data to assess chromatographic performance in production-scale protein purification columns is reported by Larson et al. (Larson, T. M., et al., Biotechnol. Prog. 19 (2003) 485-492). Moscariello, J., et al. J. Chrom. A 908 (2001) 131-141 report the characterization of the performance of industrial-scale columns. The resolution and column efficiency in chromatography is reported by Vink, H., J. Chrom. 69 (1972) 237-242. Sarker, M. and Guiochon, G., J. Chrom. A 702 (1995) 27-44 report a study of the packing behavior of axial compression columns for preparative chromatography.

SUMMARY OF THE INVENTION

With the method as reported herein a determination of the decrease in the separation efficacy and/or packing quality of a re-useable chromatography column packing can be determined without the need to use and inject a further tracer compound prior to the separation of the crude polypeptide solution for the determination of column material integrity or the need for historical data of this purification step.

The first aspect as reported herein is a method for determining whether a re-useable chromatography column packing, which is used at least for the second time in a purification step of a purification of a polypeptide, has reduced separation efficacy, e.g. compared to the separation efficacy when it was used for the first time in the same purification step of the same purification of the same polypeptide, comprising the following steps:
a) identifying and determining the experimental data of an inert change of at least one physicochemical parameter of a mobile phase passing through said re-useable chromatography column packing,
b) determining the parameters of a function of formula I by fitting the experimental data of the inert change of the physicochemical parameter of the at least second use,
c) determining the difference between the experimental data of the inert change of the physicochemical parameter of the at least second use and the function of formula I with the parameters determined in step b),
d) calculating the difference between the maximum value and the minimum value of the difference determined in step c) and normalizing said difference,
e) determining reduced separation efficacy of said re-useable chromatography column packing when the absolute value of the difference calculated in step d) is more than 0.1,
wherein the function of formula I is $$yI = \frac{1}{2}P1 \cdot \left(1 + \mathrm{erf}\left(\frac{x-m}{s \cdot \sqrt{2}}\right)\right) + A0,$$

with the amplitude P1, the starting value A0, the mean value m, the standard deviation s, and with $$\mathrm{erf}(x) = \frac{2}{\sqrt{\pi}} \sum_{0}^{\infty} \frac{(-1)^n x^{2n+1}}{(2n+1)n!}.$$

Another aspect as reported herein is a method for the chromatographic purification of a polypeptide, in which at least one chromatography step with a re-useable chromatography column packing is comprised, comprising the following steps:
a) identifying and determining the experimental data of an inert change of at least one physicochemical parameter of a mobile phase passing through said re-useable chromatography column packing,
b) determining the parameters of a function of formula I by fitting the experimental data of the inert change of the physicochemical parameter of the at least second use,
c) determining the difference between the experimental data of the inert change of the physicochemical parameter of the at least second use and the function of formula I with the parameters determined in step b),
d) calculating the difference between the maximum value and the minimum value of the difference determined in step c) and normalizing said difference, wherein the function of formula I is $$yI = \frac{1}{2}P1 \cdot \left(1 + \text{erf}\left(\frac{x-m}{s \cdot \sqrt{2}}\right)\right) + A0,$$

with the amplitude P1, the starting value A0, the mean value m, the standard deviation s, and with $$\text{erf}(x) = \frac{2}{\sqrt{\pi}} \sum_0^\infty \frac{(-1)^n x^{2n+1}}{(2n+1)n!},$$

and
further using the re-useable chromatography column packing when the absolute value of the difference calculated in step d) is 0.05 or less, or
performing additional characterization of the purified polypeptide when the absolute value of the difference calculated in step d) is more than 0.05 but less than 0.2, or
changing the re-useable chromatography column packing when the absolute value of the difference calculated in step d) is 0.2 or more.

In one embodiment said inert change of at least one physicochemical parameter of said mobile phase passing through said re-useable chromatography column packing is a significant signal change effected by the change of the concentration of a substance that does not interact with the re-useable column packing contained in said mobile phase. In another embodiment said determining the experimental data is a determining over time the experimental data of a physicochemical parameter of an inert change. In a further embodiment said inert change of at least one physicochemical parameter of a mobile phase passing through said re-useable chromatography column packing is a change of the mobile phase from 100% of a solution containing a denaturing agent to 100% of a solution not containing said denaturing agent or from 100% of a solution not containing said denaturing agent to 100% of a solution containing a denaturing agent. In another embodiment the denaturing agent is selected from sodium hydroxide, guanidinium chloride, urea, or organic solvent. In one embodiment said step c) is determining the differences between the experimental data of the inert change of the physicochemical parameter of the at least second use and the function of formula I with the parameters determined in step b) for each experimental data point. In one embodiment said signal change is a change in conductivity or in adsorption at 280 nm. In a further embodiment said inert change is a sigmoid change. In still another embodiment said at least one physicochemical parameter is determined in the conditioning or regeneration step.

DETAILED DESCRIPTION OF THE INVENTION

The first aspect as reported herein is a method for determining whether a re-useable chromatography column packing, which is used at least for the second time in a purification step of a purification of a polypeptide, has reduced separation efficacy compared to the separation efficacy when it was used for the first time in the same purification step of the same purification of the same polypeptide, comprising the following steps:

a) identifying an inert change and determining over time the experimental data of a physicochemical parameter of an inert change from 100% of a solution containing a denaturing agent to 100% of a solution not containing said denaturing agent, or vice versa, of a mobile phase passing through said re-useable chromatography column packing after the at least first use of the chromatography column packing, b) determining the parameters of a function of formula I by fitting the experimental data of the inert change of the physicochemical parameter of the at least second use obtained in a), c) determining the difference between the experimental data of the inert change of the physicochemical parameter of the at least second use and the function of formula I with the parameters determined in step b), d) calculating the difference between the maximum value and the minimum value of the difference determined in step c) and normalizing said difference, e) determining reduced separation efficacy of said re-useable chromatography column packing when the absolute value of the difference calculated in step d) is more than 0.05, wherein the function of formula I is $$yI = \frac{1}{2}P1 \cdot \left(1 + \text{erf}\left(\frac{x-m}{s \cdot \sqrt{2}}\right)\right) + A0,$$

with the amplitude P1, the starting value A0, the mean value m, the standard deviation s, and with $$\text{erf}(x) = \frac{2}{\sqrt{\pi}} \sum_0^\infty \frac{(-1)^n x^{2n+1}}{(2n+1)n!}.$$

The term "re-useable chromatography column packing" denotes a chromatography material that is packed into a chromatography column whereby the chromatography material is obtained after a purification in a not modified form, i.e. with the same characteristics as prior to the purification. A purification step denotes in general a cycle comprising the conditioning of the chromatography column packing, the application of the crude polypeptide solution, optionally the washing of the chromatography material, the recovery of the purified polypeptide from the chromatography column packing and the regeneration of the chromatography column packing. In one embodiment of the aspects as reported herein the inert change of at least one physicochemical parameter of a mobile phase passing through said re-useable chromatography column packing is a change of a physicochemical parameter over time and/or in the conditioning of the chromatography column packing and/or in the regeneration of the chromatography column packing.

The definition of a re-useable chromatography column packing as outlined above requires that all individual steps of a purification are perfectly reversible. But this is not the case. During the purification step e.g. the completely homogeneous nature of the packed chromatography material may become disturbed and the flow through the separation matrix can be compromised. At one point in time the separation efficacy and/or recovery and/or packing quality of the re-useable chromatography material is still sufficient to allow for a purification of the polypeptide from by-products but not in a purity fulfilling the requirements of the specification of said polypeptide. As a result this batch of the polypeptide maybe cannot be used as a therapeutic and has to be further treated or discarded.

With the method as reported herein a determination of the decrease in the separation efficacy and/or packing quality of and/or in the recovery from a re-useable chromatography column packing is possible without i) the need to use and inject a further tracer compound prior to the separation of the crude polypeptide solution for the determination of column material integrity or ii) the need for historical data of this purification step. Thus, the method according to the current invention allows for the determination of the quality of a re-useable chromatography column packing based on data that is generally obtained during the chromatography purification step of the polypeptide making additional steps such as tracer substance injection unnecessary.

Figure 1:
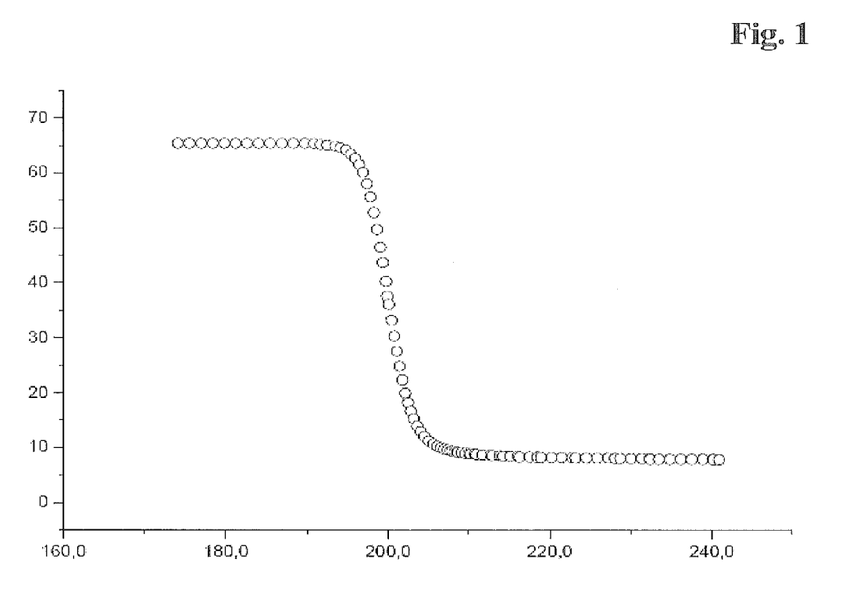
FIG. 1 Experimental data for an exemplary inert change of the conductivity for a re-useable chromatography column packing with no reduced separation efficacy/packing quality (open circles); X-axis: time [min]; Y-axis: conductivity [mS/cm].
Figure 2:
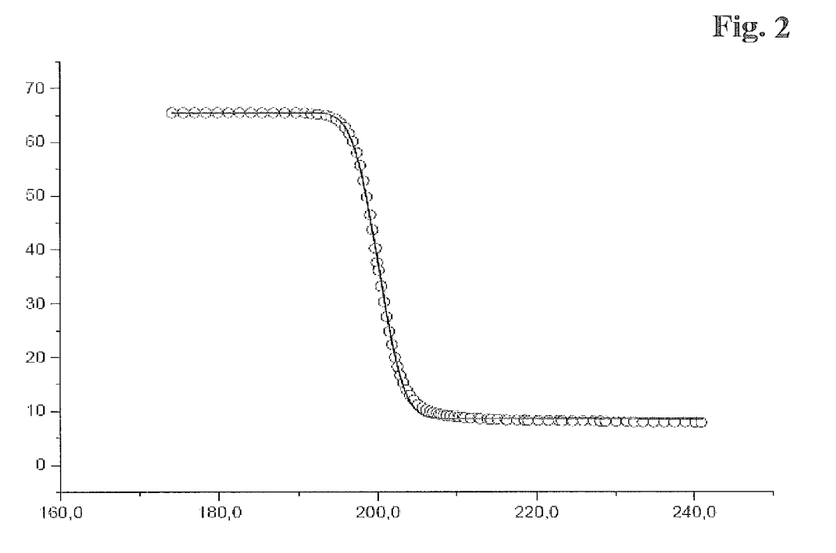
FIG. 2 Experimental data for an exemplary inert change of the conductivity for a re-useable chromatography column packing with no reduced separation efficacy/packing quality (open circles) and the fitted function according to a function of formula I; X-axis: time [min]; Y-axis: conductivity [mS/cm].
Figure 4:
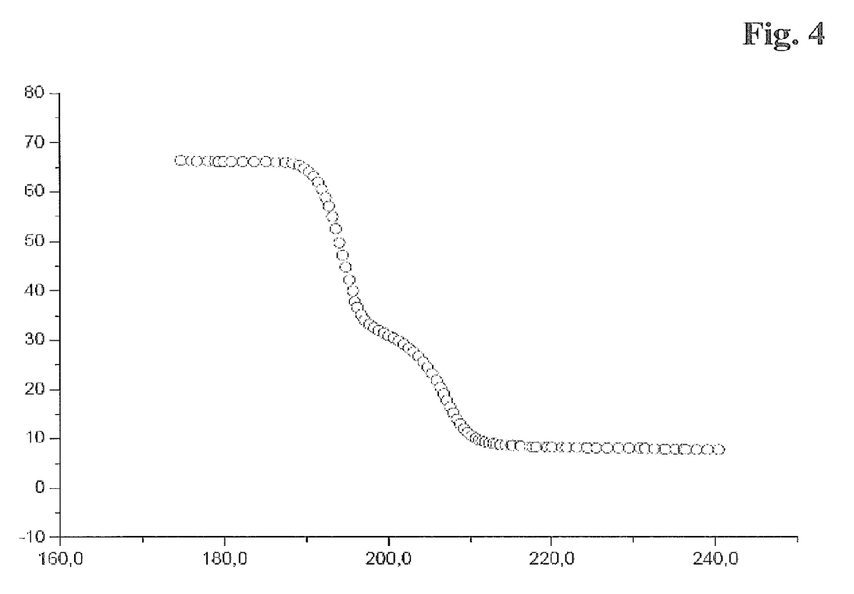
FIG. 4 Experimental data for an exemplary inert change of the conductivity for a re-useable chromatography column packing with reduced separation efficacy/packing quality (open circles); X-axis: time [min]; Y-axis: conductivity [mS/cm].
Figure 5:
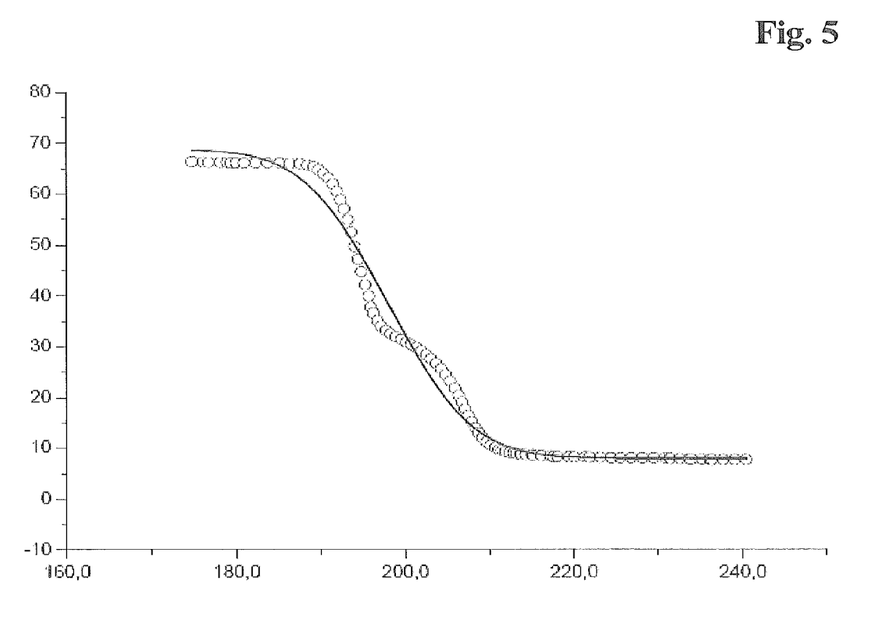
FIG. 5 Experimental data for an exemplary inert change of the conductivity for a re-useable chromatography column packing with reduced separation efficacy/packing quality (open circles) and the fitted function according to a function of formula I; X-axis: time [min]; Y-axis: conductivity [mS/cm].

The method as reported herein is based on the finding that an inert change of at least one physicochemical parameter of a mobile phase passing through a re-useable chromatography column packing during the purification of a polypeptide can be used for determining the chromatography material separation efficacy and/or packing quality. Such an "inert change" is the change of at least one, preferably one, physicochemical parameter over time, such as the concentration of a substance contained in the mobile phase, or of the mobile phase itself during the purification step. The substance does not interact with the functionality of the chromatography material effecting the purification of the polypeptide. Exemplary inert changes of at least one physicochemical parameter of a mobile phase passing through said re-useable chromatography column packing are i) a change from denaturing conditions to non-denaturing conditions, or ii) a change from strongly alkaline conditions to buffered conditions, or iii) a change from organic solvent to water. In one embodiment the change is from 100% of a 0.5 to 1 M sodium hydroxide solution or a 5 M guanidinium chloride solution or an 8 M urea solution or organic solvent to 100% buffer or 100% water, optionally comprising an ionizing agent such as trifluoro acetic acid in up to 1% (v/v). Or vice versa the changes is i) from non-denaturing conditions to denaturing conditions, or ii) from buffered conditions to strongly alkaline conditions, or iii) from water to organic solvent. In another embodiment the change is from 100% buffer or 100% water, optionally comprising an ionizing agent such as trifluoro acetic acid in up to 1% (v/v), to 100% of a 0.5 to 1 M sodium hydroxide solution, or to 100% of a 5 M guanidinium chloride solution, or to 100% of an 8 M urea solution or organic solvent. A chromatogram for an inert change showing no reduction in separation efficacy/packing quality is shown in FIG. 1 and a chromatogram for an inert change showing a reduction in separation efficacy/packing quality is shown in FIG. 4.

In one embodiment the inert change of the at least one physicochemical parameter over time is determined by the experimental data recorded during the purification, such as the absorption at 280 nm, or the conductivity of the mobile phase leaving the chromatography column, or the organic solvent concentration leaving the chromatography column.

The term "mobile phase" denotes a liquid that is used in column chromatography and that surrounds the chromatography material of the chromatography column packing, which in turn is the stationary phase.

It has been found that from a comparison of the experimental data recorded during the inert change of the at least second use of said re-useable chromatography column packing with the recorded data during the inert change of the at least second use of said re-useable chromatography column packing fitted to the function of formula I a determination of the separation efficacy/packing quality of the re-useable chromatography column packing can be obtained. In one embodiment the experimental data is recorded during the at least second purification of said polypeptide with a column packing made with chromatography material that has been used one or more times in the same purification steps of the same purification of the same polypeptide prior to this use. The function of formula I is as follows:

$$yI = \frac{1}{2}P1 \cdot \left(1 + \mathrm{erf}\left(\frac{x-m}{s \cdot \sqrt{2}}\right)\right) + A0,$$

with
the amplitude P1,
the starting value A0,
the mean value m,
the standard deviation s,
and with $$\mathrm{erf}(x) = \frac{2}{\sqrt{\pi}} \sum_0^\infty \frac{(-1)^n x^{2n+1}}{(2n+1)n!}.$$

The methods as reported herein employ the integrated form of the Gaussian distribution yielding quality attributes for the packing of the column. With the function of formula I the deviation from a purely diffusion controlled distribution mechanism of a compound(s) contained in an approximately rectangular pulse of said compound(s) at the column inlet can be determined. This is achieved by comparing the function of formula I fitted to the experimental data recorded during the identified inert change in the purification of the polypeptide with the recorded experimental data itself, whereby the difference during the inert change of the fitted function and the not-fitted experimental data should not exceed a predetermined threshold in order to provide a purified polypeptide of desired characteristics.

The comparison is done by calculating the difference between the experimental data with which the function of formula I has been fitted and the fitted function of formula I. In order to make the results of individual purifications comparable to each other the results or the difference are normalized, e.g. by dividing the value with the maximum value of the experimental data of said physicochemical parameter during said inert change. In one embodiment said normalization is by a division with the value of the parameter A0 of the fitted function of formula I. In one embodiment a normalized difference function, as shown in the following formula II, is used:

$$yII = \left(x - \left(\frac{1}{2}P1 \cdot \left(1 + \mathrm{erf}\left(\frac{x-m}{s \cdot \sqrt{2}}\right)\right) + A0\right)\right)\bigg/ A0.$$

Thus, in one embodiment step b) reads: determining the parameters of a function of formula I by fitting the experimental data of the inert change of the physicochemical parameter of the at least second use and determining therewith also the parameters of a normalized difference function of formula II, and step c) reads: determining the difference between the experimental data of the inert change of the physicochemical parameter of the at least second use and the function of formula II with the parameters determined in step b). In another embodiment said normalization is in the step of calculating the difference between the maximum value and the minimum value of the difference determined between the experimental data and the function of formula I fitted to said experimental data by normalizing said difference by dividing said difference with the maximum value of the experimental data of said physicochemical parameter during said inert change.

Figure 3:
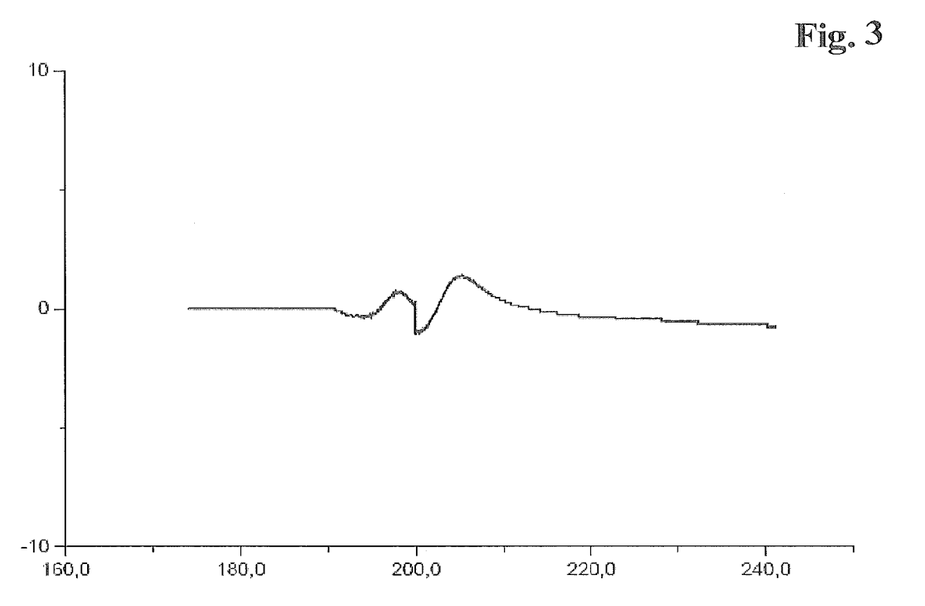
FIG. 3 Absolute difference between the experimental data for an exemplary inert change of the conductivity for a re-useable chromatography column packing with no reduced separation efficacy/packing quality (open circles) and the fitted function according to formula I; X-axis: time; Y-axis: difference.
Figure 6:
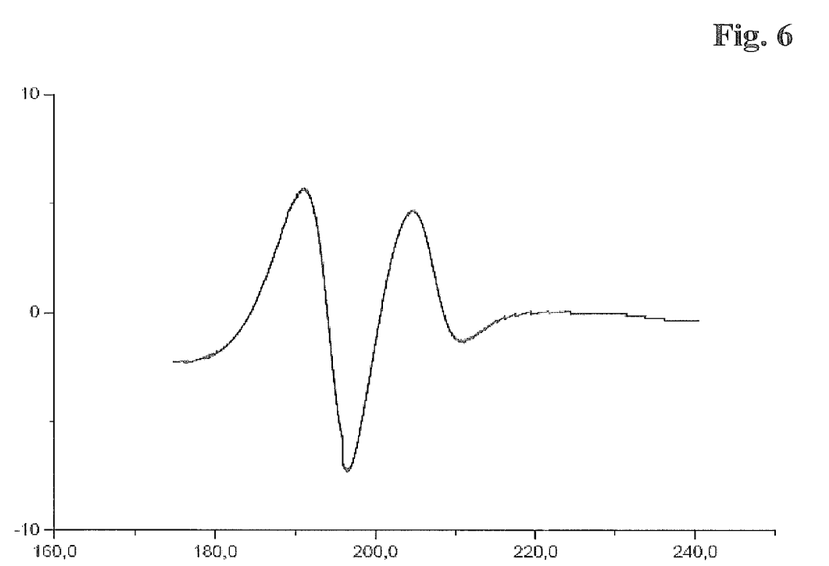
FIG. 6 Absolute difference between the experimental data for an exemplary inert change of the conductivity for a re-useable chromatography column packing with reduced separation efficacy/packing quality (open circles) and the fitted function according to a function of formula I; X-axis: time [min]; Y-axis: difference [mS/cm].

An exemplary difference function for a chromatogram for an inert change with no reduction in separation efficacy and/or packing quality is shown in FIG. 3 and for a chromatogram for an inert change with a reduction in separation efficacy and/or packing quality is shown in FIG. 6.

For the calculation of the absolute difference value the global maximum and the global minimum of the difference between the experimental data and the fitted experimental data calculated for each experimental data point is determined. The difference between this maximum value and this minimum value is calculated and provides a parameter with which the packing quality of the re-useable chromatography column packing can be determined. In one embodiment said difference is normalized by dividing the calculated difference values with the maximum value of the experimental data used for the calculation.

Depending on the polypeptide to be purified and its characteristics to be achieved threshold values for the absolute difference between the maximum value and the minimum value of the difference function can be given whereby the individual exceeding of each of the threshold values results in an action to be performed. In one embodiment said difference between the maximum value and the minimum value of the normalized difference function can be accepted and the packing can be used further if the absolute value of the difference calculated is less than 0.2 or 0.1 or 0.05. In one embodiment said difference between the maximum value and the minimum value of the normalized difference can be accepted but additional analyses and/or assessments have to be performed to ensure the specification conformity of the purified polypeptide if the absolute value is 0.05 or more but less than 0.2, or 0.1 or more but less than 0.2, or 0.1 or more but less than 0.15. In one embodiment said difference between the maximum value and the minimum value of the normalized difference cannot be accepted and the packing has to be changed/renewed if the absolute value is 0.2 or more, or 0.15 or more.

Therefore, another aspect as reported herein is a method for the chromatographic purification of a polypeptide, wherein at least one chromatography step is contained which employs a re-useable chromatography column packing, characterized in that said method comprises the following steps:
a) identifying and determining the experimental data of an inert change of at least one physicochemical parameter of a mobile phase passing through said re-useable chromatography column packing,
b) determining the parameters of a function of formula I by fitting the experimental data of the inert change of the physicochemical parameter of the at least second use,
c) determining the difference between the experimental data of the inert change of the physicochemical parameter of the at least second use and the function of formula I with the parameters determined in step b),
d) calculating the difference between the maximum value and the minimum value of the difference determined in step c) and normalizing said difference, wherein the function of formula I is $$yI = \frac{1}{2}P1 \cdot \left(1 + \mathrm{erf}\left(\frac{x-m}{s \cdot \sqrt{2}}\right)\right) + A0,$$

with the amplitude P1, the starting value A0, the mean value m, the standard deviation s, and with $$\mathrm{erf}(x) = \frac{2}{\sqrt{\pi}} \sum_0^\infty \frac{(-1)^n x^{2n+1}}{(2n+1)n!},$$

and
further using the re-useable chromatography column packing when the absolute value of the difference calculated in step d) is 0.05 or less, or
performing additional assessment and/or characterization of the purified polypeptide when the absolute value of the difference calculated in step d) is 0.05 or more but less than 0.2, or
changing the re-useable chromatography column packing when the absolute value of the difference calculated in step d) is 0.2 or more.

A "polypeptide" is a polymer consisting of amino acids joined by peptide bonds, whether produced naturally or synthetically. Polypeptides of less than about 20 amino acid residues may be referred to as "peptide", whereas molecules consisting of two or more polypeptides or comprising one polypeptide of more than 100 amino acid residues may be referred to as "protein". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

In one embodiment said polypeptide is recombinantly produced. In another embodiment said polypeptide is an immunoglobulin or an immunoglobulin conjugate. The term "immunoglobulin" refers to a protein consisting of one or more polypeptide(s) substantially encoded by immunoglobulin genes. The recognized immunoglobulin genes include the different constant region genes as well as the myriad immunoglobulin variable region genes. Immunoglobulins may exist in a variety of formats, including, for example, Fv, Fab, and F(ab)$_2$ as well as single chains (scFv) or diabodies (e.g. Huston, J. S., et al., Proc. Natl. Acad. Sci. USA 85 (1988) 5879-5883; Bird, R. E., et al., Science 242 (1988) 423-426; in general, Hood, L. E., et al., Immunology, Benjamin N. Y., 2nd edition (1984); and Hunkapiller, T. and Hood, L. E., Nature 323 (1986) 15-16). The term "immunoglobulin conjugate" denotes a polypeptide comprising at least one domain of an immunoglobulin heavy or light chain conjugated via a peptide bond to a further polypeptide. The further polypeptide is either a non-immunoglobulin peptide, such as a hormone, or growth receptor, or antifusogenic peptide, or complement factor, or the like, or an immunoglobulin fragment, such as Fv, Fab, and F(ab)$_2$ as well as single chain antibody (scFv) or diabody.

Methods for purifying polypeptides and immunoglobulins are well established and widespread used and are employed either alone or in combination. Such methods are, for example and in certain embodiments, affinity chromatography using microbial-derived proteins (e.g. protein A or protein G affinity chromatography), ion exchange chromatography (e.g. cation exchange (carboxymethyl resins), anion exchange (amino ethyl resins) and mixed-mode exchange chromatography), thiophilic adsorption (e.g. with beta-mercaptoethanol and other SH ligands), hydrophobic interaction or aromatic adsorption chromatography (e.g. with phenylsepharose, aza-arenophilic resins, or m-aminophenylboronic acid), metal chelate affinity chromatography (e.g. with Ni(II)- and Cu(II)-affinity material), size exclusion chromatography, and preparative electrophoretic methods (such as gel electrophoresis, capillary electrophoresis) (Vijayalakshmi, M. A., Appl. Biochem. Biotech. 75 (1998) 93-102). In one embodiment said chromatography column packing is a chromatography material selected from an affinity chromatography material, or an ion exchange chromatography material, or a thiophilic adsorption chromatography material, or a hydrophobic interaction chromatography material, or an aromatic adsorption chromatography material, or a metal chelate affinity chromatography material, or a size exclusion chromatography material.

In another embodiment the method as reported herein is used for the determination if the process hardware except the chromatography material has reduced separation efficacy.

The following examples and figures are provided to aid the understanding of the present invention, the true scope of which is set forth in the appended claims. As the polypeptide erythropoietin was available in sufficient quantities in our laboratory at the time the invention was made the invention is exemplified with this polypeptide. This should not be understood as limitation but only as an example of the invention. It is understood that modifications can be made in the procedures set forth without departing from the spirit of the invention.

EXAMPLE 1

Fermentation and Purification of Erythropoietin

Erythropoietin can be produced and purified e.g. according to WO 01/87329.

The purification comprises some chromatography steps. One of these is a Blue Sepharose chromatography. Blue Sepharose consists of Sepharose beads to the surface of which the Cibacron blue dye is covalently bound. Since erythropoietin binds more strongly to Blue Sepharose than most non-proteinaceous contaminants, some proteinaceous impurities and PVA, erythropoietin can be enriched in this step. The elution of the Blue Sepharose column is performed by increasing the salt concentration as well as the pH. The column is filled with Blue Sepharose, regenerated with NaOH and equilibrated with equilibration buffer (sodium/calcium chloride and sodium acetate). The acidified and filtered fermenter supernatant is loaded. After completion of the loading, the column is washed first with a buffer similar to the equilibration buffer containing a higher sodium chloride concentration and consecutively with a TRIS-base buffer. The product is eluted with a TRIS-base buffer and collected in a single fraction in accordance with the master elution profile.

During the equilibration, separation, and regeneration step of the chromatography cycle the conductivity of the mobile phase at the outlet of the column is determined and recorded with a standard conductivity measuring device.

EXAMPLE 2

Change in Column Properties

Figure 7:
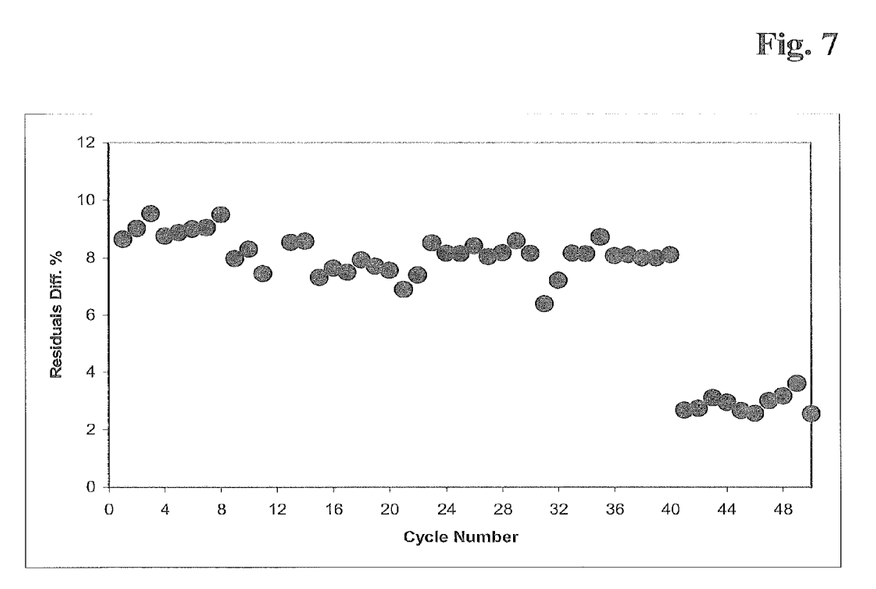
FIG. 7 Monitoring of column integrity with a method as reported herein over 50 chromatographic cycles using formula II.

The column can be monitored over the process continuously using the method as reported herein. Subtle changes become detectable independently of changes of other process parameters. In FIG. 7 a change in the column packing resulting in a change in the separation properties is shown. The change occurred after cycle 40.

Figure 8:
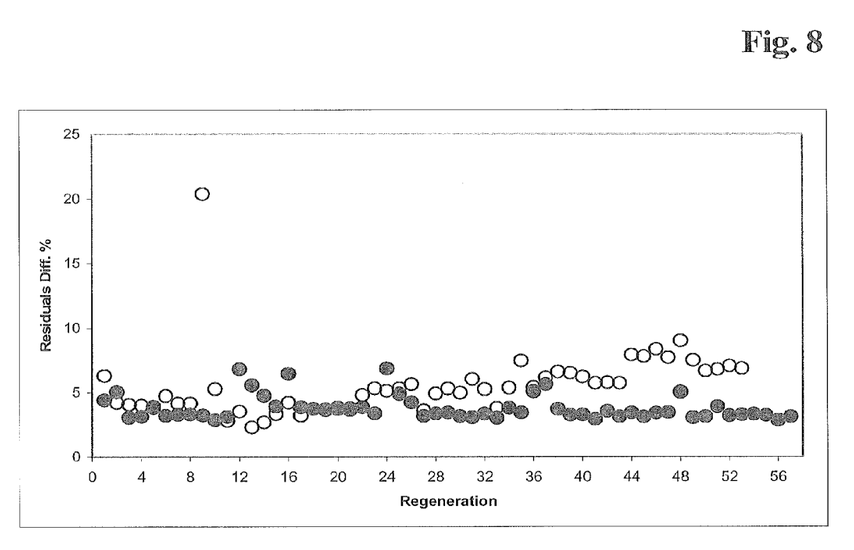
FIG. 8 Monitoring of column integrity with a method as reported herein using formula II.
  Full circles: parameter derived for regeneration of column without changes in column packing.
  Open circles: parameter derived for regeneration of column with a cracked bed during regeneration cycle No. 9.

In the case of a column with a broken bed, the quality of the fit decreases dramatically, as seen in the derived parameter residuals difference as shown in cycle 9 of FIG. 8 (open circles).

The invention claimed is:
1. A method for determining whether a re-useable chromatography column packing, which is used at least for the second time in a purification step of a purification of a polypeptide, has reduced separation efficacy in said purification step of said purification of said polypeptide, wherein said method comprises the following steps:
   a) identifying and determining the experimental data of an inert change of at least one physicochemical parameter of a mobile phase passing through said re-useable chromatography column packing of the at least second use,
b) determining the parameters of a function of formula I by fitting the experimental data of the inert change of the physicochemical parameter of the at least second use,
c) determining the difference between the experimental data of the inert change of the physicochemical parameter of the at least second use and the function of formula I with the parameters determined in step b),
d) calculating the difference between the maximum value and the minimum value of the difference determined in step c) and normalizing said difference,
e) determining reduced separation efficacy of said re-useable chromatography column packing when the absolute value of the difference calculated in step d) is more than 0.1,
wherein the function of formula I is $$yI = \frac{1}{2}P1 \cdot \left(1 + \text{erf}\left(\frac{x-m}{s \cdot \sqrt{2}}\right)\right) + A0,$$

with the amplitude P1, the starting value A0, the mean value m, the standard deviation s, and with $$\text{erf}(x) = \frac{2}{\sqrt{\pi}} \sum_{0}^{\infty} \frac{(-1)^n x^{2n+1}}{(2n+1)n!}.$$

2. The method according to claim 1, wherein said inert change is recorded during the purification by a standard conductivity measuring device.

3. The method according to claim 1 wherein said inert change is recorded during the purification by a standard adsorption measuring device.

4. The method according to claim 1, wherein said inert change of at least one physicochemical parameter of a mobile phase passing through said re-useable chromatography column packing is a change effected by the change of the concentration of a substance in the mobile phase that does not interact with the re-useable column packing.

5. The method according to claim 1, wherein said inert change is a change in conductivity, as measured by a standard conductivity measuring device.

6. The method according to claim 1, wherein said inert change of at least one physicochemical parameter of a mobile phase passing through said re-useable chromatography column packing is a change of from 100% of a solution containing a denaturing agent to 100% of a solution not containing said denaturing agent, or vice versa.

7. The method according to claim 6, wherein said denaturing agent is selected from sodium hydroxide, guanidinium chloride, urea or organic solvent.

8. The method according to claim 1, wherein said inert change is a sigmoid change.

9. The method according to claim 1, wherein said inert change is a change over time.

10. A method for the chromatographic purification of a polypeptide, wherein at least one chromatography step using a re-useable chromatography column packing is contained, wherein said method comprises the following steps:
a) identifying and determining the experimental data of an inert change of at least one physicochemical parameter of a mobile phase passing through said re-useable chromatography column packing of the at least second use,
b) determining the parameters of a function of formula I by fitting the experimental data of the inert change of the physicochemical parameter of the at least second use,
c) determining the difference between the experimental data of the inert change of the physicochemical parameter of the at least second use and the function of formula I with the parameters determined in step b),
d) calculating the difference between the maximum value and the minimum value of the difference determined in step c) and normalizing said difference,
wherein the function of formula I is $$yI = \frac{1}{2}P1 \cdot \left(1 + \text{erf}\left(\frac{x-m}{s \cdot \sqrt{2}}\right)\right) + A0,$$

with the amplitude P1, the starting value A0, the mean value m, the standard deviation s, and with $$\text{erf}(x) = \frac{2}{\sqrt{\pi}} \sum_{0}^{\infty} \frac{(-1)^n x^{2n+1}}{(2n+1)n!},$$

and
further using the re-useable chromatography column packing when the absolute value of the difference calculated in step d) is 0.05 or less, or
performing an additional characterization and/or assessment of the purified polypeptide when the absolute value of the difference calculated in step d) is more than 0.05 but less than 0.2, or
changing the re-useable chromatography column packing when the absolute value of the difference calculated in step d) is 0.2 or more.

11. The method according to claim 10, wherein said inert change is recorded during the purification by a standard conductivity measuring device.

12. The method according to claim 10, wherein said inert change is recorded during the purification by a standard adsorption measuring device.

13. The method according to claim 10, wherein said inert change of at least one physicochemical parameter of a mobile phase passing through said re-useable chromatography column packing is a change effected by the change of the concentration of a substance in the mobile phase that does not interact with the re-useable column packing.

14. The method according to claim 10, wherein said inert change is a change in conductivity, as measured by a standard conductivity measuring device.

15. The method according to claim 10, wherein said inert change of at least one physicochemical parameter of a mobile phase passing through said re-useable chromatography column packing is a change of from 100% of a solution containing a denaturing agent to 100% of a solution not containing said denaturing agent, or vice versa.

16. The method according to claim 15, wherein said denaturing agent is selected from sodium hydroxide, guanidinium chloride, urea or organic solvent.

17. The method according to claim 10, wherein said inert change is a sigmoid change.

18. The method according to claim 10, wherein said inert change is a change over time.

* * * * *